US008709810B2

(12) United States Patent
Pressi et al.

(10) Patent No.: US 8,709,810 B2
(45) Date of Patent: Apr. 29, 2014

(54) **PREPARATION AND USE OF MERISTEMATIC CELLS BELONGING TO THE *DENDROBIUM PHALAENOPSIS, ANSELLIA, POLYRRHIZA, VANILLA, CATTLEYA* AND *VANDA* GENERA WITH HIGH CONTENT OF PHENYLPROPANOIDS, HYDROSOLUBLE POLYSACCHARIDES AND EXTENSINS**

(75) Inventors: Giovanna Pressi, Altavilla Vicentina (IT); Roberto Dal Toso, Altavilla Vicentina (IT); Elena Sgaravatti, Altavilla Vicentina (IT)

(73) Assignee: I.R.B. Istituto di Ricerche Biotechnologiche S.r.l., Altavilla Vicentina (IT)

( * ) Notice: Subject to any disclaimer, the term of this patent is extended or adjusted under 35 U.S.C. 154(b) by 23 days.

(21) Appl. No.: 13/294,933

(22) Filed: Nov. 11, 2011

(65) Prior Publication Data

US 2013/0022580 A1 Jan. 24, 2013

Related U.S. Application Data

(63) Continuation-in-part of application No. 13/189,199, filed on Jul. 22, 2011, now abandoned.

(51) Int. Cl.
*C12N 5/00* (2006.01)
*C12N 5/02* (2006.01)

(52) U.S. Cl.
USPC .......................... 435/410; 435/420; 435/431

(58) Field of Classification Search
USPC ......................................... 435/410, 420, 431
See application file for complete search history.

(56) References Cited

U.S. PATENT DOCUMENTS

| 3,514,900 | A | | 6/1970 | McDade |
| 5,443,855 | A | * | 8/1995 | Wolf et al. .................... 424/401 |
| PP13,562 | P2 | | 2/2003 | Asai |
| 2010/0022470 | A1 | | 1/2010 | Wu |

FOREIGN PATENT DOCUMENTS

| EP | 0 533 408 B2 | 2/2001 |
| KR | 10-2007-0117355 | 12/2007 |
| WO | WO 2009/139231 A1 | 11/2009 |

OTHER PUBLICATIONS

Funk et al. "Influence of Growth Regulators and an Elicitor on Phenylpropanoid Metabolism in Suspension Cultures of *Vanilla planifolia*," Phytochemistry (1990), vol. 29, No. 3, pp. 845-848.*
Philip et al. "In vitro Transformation of Root meristem to Shoot and Plantlets in *Vanilla planifolia*," Annals of Botany (1988), 61, pp. 193-199.*
Korkina, L.G. "Phenylpropanoids as Naturally Occurring Antioxidants: From Plant Defense to Human Health," Cellular and Molecular Biology (2007), 53, No. 1, pp. 15-25.*
Jarvis et al. A Survey of the Pectic Content of Nonlignified Monocot Cell Walls (1988), Plant Physiol., 88, pp. 309-314.*
K. H. Tan et al., "Floral Phenylpropanoid Cocktail and Architecture of *Bulbophyllum vinaceum* Orchid in Attracting Fruit Flies for Pollination," J. Chem. Ecol., vol. 32, pp. 2429-2441, 2006.
M. B. Ali et al., "Enhancement of Phenylpropanoid Enzymes and Lignin in *Phalaenopsis* Orchid and Their Influence on Plant Acclimatisation at Different Levels of Photosynthetic Photon Flux," Plant Growth Regul, vol. 49, pp. 137-146, 2006.
R. Gebhardt, "Antioxidative and Protective Properties of Extracts from Leaves of the Artichoke (*Cynara scolymus* L.) Against Hydroperoxide-Induced Oxidative Stress in Cultured Rat Hepatocytes," Toxicology and Applied Pharmacology, vol. 144, pp. 279-286, 1997.
F.Perez-Garcia et al., "Activity of Artichoke Leaf Extract on Reactive Oxygen Species in Human Leukocytes," Free Rad. Res., vol. 33, pp. 661-665, 2000.
J.E. Brown et al., "Luteolin-Rich Artichoke Extract Protects Low Density Lipoprotein from Oxidation in Vitro," Free Rad. Res., vol. 29, pp. 247-255, 1998.
K. Kraft, "Artichoke Leaf Extract—Recent Findings Reflecting Effects on Lipid Metabolism, Liver and Gastrointestinal Tracts," Phytomedicine, vol. 4, No. 4, pp. 369-378, 1997.
M.H. Pittler et al., "Artichoke Leaf Extract for Serum Cholesterol Reduction," Perfusion, vol. 11, pp. 338-340, 1998.
Dogan et al., Characterization and Purification of Polyphenol Oxidase from Artichoke (*Cynara scolymus* L.), J. Agric. Food Chem., vol. 53, pp. 776-785, 2005.
B. McDougall et al., "Dicaffeoylquinic and Dicaffeoyltartaric Acids are Selective Inhibitors of Human Immunodeficiency Virus Type 1 Integrase," Antimicrobial Agents and Chemotherapy, vol. 42, No. 1, pp. 140-146, Jan. 1998.
J. Slanina et al., "New and Facile Method of Preparation of the Anti-HIV-1 Agent, 1,3-Dicaffeoylquinic Acid," Tetrahedron Letters, vol. 42, pp. 3383-3385, 2001.
A.J. Mossi et al., "Identification and Characterization of Antimicrobial Components in Leaf Extracts of Globe Artichoke (*Cynara scolymus* L.), "Acta Hort., vol. 501, pp. 111-114, 1999.
X.F. Zhu et al., "Antifungal Activity of *Cynara scolymus* L. Extracts," Fitoterapia, vol. 76, pp. 108-111, 2005.
L.G. Korkina, "Phenylpropanoids as Naturally Occurring Antioxidants: From Plant Defense to Human Health," Cellular and Molecular Biology, vol. 53, No. 1, pp. 15-25, 2007.
R. Kurata et al., "Growth Suppression of Human Cancer Cells by Polyphenolics from Sweetpotato (*Ipomoea batatas* L.) Leaves, " J. Agric. Food Chem., vol. 55, pp. 185-190, 2007.
X.-Q. Zha et al., "Induction of Immunomodulating Cytokines by Polysaccharides from *Dendrobium huoshanense*," Pharmaceutical Biology, vol. 45, No. 1, pp. 71-76, 2007.

(Continued)

*Primary Examiner* — Susan McCormick Ewoldt
(74) *Attorney, Agent, or Firm* — Dickstein Shapiro LLP (57) ABSTRACT

The present invention relates to the preparation of plant cell cultures belonging to the *Dendrobium Phalaenopsis, Ansellia, Polyrrhiza, Vanilla, Cattleya* and *Vanda* genera and their use in cosmetic, nutritional and pharmaceutical fields. In particular, the present invention regards a selected cell culture of meristematic cells of plants belonging to the *Dendrobium Phalaenopsis, Ansellia, Polyrrhiza, Vanilla, Cattleya* and *Vanda* genera characterized in that it contains an amount of phenylpropanoids greater than 0.1% expressed on the cell dry weight and an amount of hydrosoluble polysaccharides greater than 5% expressed on the cell dry weight, as well as preparations, pharmaceutical and cosmetic compositions or food supplements containing the cell culture.

13 Claims, 4 Drawing Sheets

(56) References Cited

OTHER PUBLICATIONS

A. Luo et al., "In Vitro Antioxidant Activities of a Water-Soluble Polysaccharide Derived from *Dendrobium nobile* Lindl. Extracts," International Journal of Biological Macromolecules, vol. 45, pp. 359-363, 2009.

Y. Fan et al., "Composition Analysis and Antioxidant Activity of Polysaccharide from *Dendrobium denneanum*," International Journal of Biological Macromolecules, vol. 45, pp. 169-173, 2009.

X.-Q. Zha et al., "Production Stability of Active Polysaccharides of *Dendrobium huoshanense* Using Long-term Cultures of Protocorm-Like Bodies," Planta Med., vol. 74, pp. 90-93, 2008.

Tokuhara et al., "Highly-Efficient Somatic Embryogenesis from Cell Suspension Cultures of *Phalaenopsis* Orchids by Adjusting Carbohydrate Sources," in Vitro Cell. Dev. Biol.-Plant, vol. 39, pp. 635-639, Nov.-Dec. 2003.

B. R. Shrestha et al., "Plant Regeneration from Cell Suspension-Derived Protoplasts of *Phalaenopsis*," Plant Cell Rep., vol. 26, pp. 719-725, 2007.

K. Tokuhara et al., "Induction of Embryogenic Callus and Cell Suspension Culture from Shoot Tips Excised from Flower Stalk Buds of *Phalaenopsis* (Orchidaceae)," In Vitro Cell. Dev. Biol.—Plant, vol. 37, pp. 457-461, Jul.-Aug. 2001.

C. funk et al., "Influence of Growth Regulators and an Elicitor on Phenylpropanoid Metabolism in Suspension Cultures of *Vanilla planifolia*," Phytochemistry, vol. 29, No. 3, pp. 845-848, 1990.

S. Kaur et al., "In Vitro Propagation of *Vanda testacea* (Lindl.) Reichb.f.—A Rare Orchid of High Medicinal Value," Plant Tissue Cult. & Biotech., vol. 19, No. 1, pp. 1-7, Jun. 2009.

Y. Hsieh, et al., "Structure and Bioactivity of the Polysaccharides in Medicinal Plant *Dendrobium huoshanense*," Bioorganic & Medicinal Chemistry, vol. 16, pp. 6054-6068, 2008.

A. Luo et al., "Purification, Composition Analysis and Antioxidant Activity of the Polysaccharides from *Dendrobium nobile* Lindl.," Carbohydrate Polymers, vol. 79, pp. 1014-1019, 2010.

J.-H. Wang et al., "Comparison of Antitumor Activities of Different Polysaccharide Fractions from the Stems of *Dendrobium nobile* Lindl.," Carbohydrate Polymers, vol. 79, pp. 114-118, 2010.

J. D. Bythrow, "Vanilla as a Medicinal Plant," Seminars in Integrative Medicine, vol. 3, pp. 129-131, 2005.

B.S. Nayak et al., "Evaluation of Wound Healing Activity of *Vanda roxburghii* R.Br. (Orchidacea): A Preclinical Study in a Rat Model," Lower Extremity Wounds, vol. 4, No. 4, pp. 200-204, 2005.

M. Chinsamy et al., "Pharmacological Evaluation as a Tool in South African Orchid Conservation," SAAB Annual Meeting Abstracts, p. 395, 2009.

R. Gutiérrez, "Orchids: A Review of Uses in Traditional Medicine, Its Phytochemistry and Pharmacology," Journal of Medicinal Plants Research, vol. 4, No. 8, pp. 592-638, Apr. 18, 2010.

\* cited by examiner

FIG 1: antioxidant activity by glycerolic stems of *Dendrobium farmeri* (DfSG)

Fattore di diluizione = diluition factor

% riduzione = reduction %

FIG 2: inhibition activity of the production of nitric oxide (NO) by spray dried stems of *Dendrobium polysema* (DpSD)

| | % NO |
|---|---|
| LPS 20µg/mL | 100 |
| DpSD 10µg/mL | 100 |
| DpSD 100µg/mL | 96,1 |
| DpSD 250µg/mL | 74,5 |
| DpSD 500µg/mL | 63,2 |

FIG 3: inhibition activity of the production of nitric oxide (NO) by spray dried stems of *Vanda coerulea* (VcSD)

| | % NO |
|---|---|
| LPS 20µg/mL | 100 |
| VcSD 10µg/mL | 100 |
| VcSD 100µg/mL | 93,8 |
| VcSD 250µg/mL | 71,4 |
| VcSD 500µg/mL | 59,7 |

FIG 4: inhibition activity of the production of nitric oxide (NO) by lyophilized stems of *Vanilla planifolia* (VpSL)

| | % NO |
|---|---|
| LPS 20µg/mL | 100 |
| VpSL 10µg/mL | 98,6 |
| VpSL 100µg/mL | 87,2 |
| VpSL 250µg/mL | 66,2 |
| VpSL 500µg/mL | 51,9 |

FIG 5: inhibition activity of the collagenase by lyophilic stems of *Dendrobium nobile* (DnSL)

| | % inibizione collagenasi |
|---|---|
| CTRL+enzima | 100 |
| CTRL-enzima | 0 |
| DnSL 0,5mg/mL | 65,32 |
| DnSL 1mg/mL | 72,86 |

FIG 6: inhibition activity of the collagenase by lyophilic stems of *Cattleya labiata* (ClSL)

% inibizione collagenasi = Collagenase inhibition

PREPARATION AND USE OF MERISTEMATIC CELLS BELONGING TO THE *DENDROBIUM PHALAENOPSIS, ANSELLIA, POLYRRHIZA, VANILLA, CATTLEYA* AND *VANDA* GENERA WITH HIGH CONTENT OF PHENYLPROPANOIDS, HYDROSOLUBLE POLYSACCHARIDES AND EXTENSINS

This is a continuation-in-part of application Ser. No. 13/189,199, filed Jul. 22, 2011, now abandoned.

BACKGROUND OF THE INVENTION

1. Field of the Invention

The present invention regards the preparation of plant cell cultures belonging to the *Dendrobium Phalaenopsis, Ansellia, Polyrrhiza, Vanilla, Cattleya* and *Vanda* genera and their use in cosmetic, nutritional and pharmaceutical fields.

2. Description of the Related Art

The plants of the *Dendrobium* and *Phalaenopsis* genera belong to the Orchidaceae family. The Orchidaceae family is the second largest in the plant world after the Compositeae family and comprises about 735 genera divided into 25000 species. The Orchids of the *Dendrobium, Phalaenopsis, Ansellia, Polyrrhiza, Vanilla, Cattleya* and *Vanda* genera are epiphyte plants, i.e. they live on trees and grow on ligneous substrates. The epiphyte orchids, widespread in the Tropics, live fixed to forest trees, have a stalk with isolated or reduced, scale-like leaves and often have long sloping aerial roots, enclosed in the velamen which constitutes a sleeve with absorbing function around the root and with green photosynthesizing apex.

Numerous rare, dying species belong to the *Dendrobium, Phalaenopsis, Ansellia, Polyrrhiza, Vanilla, Cattleya* and *Vanda* genera, and as such they are protected from indiscriminate collection.

Numerous bioactive compounds have been isolated and identified in many orchid species. Tan Keng Hong et al (Journal of Chemical Ecology, 2006, 32(11):2429-2441) describe the presence of numerous phenylpropanoids in the flowers of *Bulbophyllum vinaceum*, while Ali Mohammad Babar et al (Plant Growth Regulation, 2006, 49(2-3): 137-146) report an increase of the phenylpropanoid synthesis in seedlings of *Phalaenopsis* in response to radiation-induced stress. The biological activities of phenylpropanoids have been widely described in the literature. In particular, these compounds are involved in the protection of proteins, lipids and nucleic acids from damage caused by free radicals (Gebhardt R. et al, 1997, Toxicol. Appl. Pharm. 144:279-286; Perez Garcia F. et al, 2000, Free Radical Res., 33: 661-665); they inhibit the biosynthesis of cholesterol, contribute to the prevention of atherosclerosis and of vascular disorders (Brown J. E. Et al, 1998, Free Radical Res., 29:247-255; Kraft K., 1997, 4: 369-378; Pittlern M H et al, Perfusion, 11:338-340), have hepaprotective, choleretic and diuretic activities (Dogan S. et al, 2005, J. Agric. Food Chem., 53:776-785), antiviral activities against HIV (Mcdougall B. et al, 1998, Antimicrob. Agents Ch., 42: 140-146; Shanina J. et al, 2001, Tetrahedron Lett., 42:3383-3385), antibacterial and antifungal activities (Martinov et al, 1999, Acta Horticulturae, 501:111-114; Zhu X F, 2005, Fitoterapia; 76: 108-111), anti-inflammatory and cicatrizing activities (Korkina et al., 2007, Cellular and Molecular Biology 53(5): 78-83) and potential tumor protection activities (Kurata R. et al, 2007, J. Agric. Food Chem. 55(1):185-190).

Several works in the literature show that hydrosoluble polysaccharides extracted from orchid plants belonging to the *Dendrobium* genus exert considerable immunomodulating and antioxidant activities (Zha, Xue-Qiang et al, 2007, Pharmaceutical Biology 45(1): 71-76; Luo A. et al, 2009, Int. J. Biol. Macromol. 45(4):359-63; Fan Y. Et al, 2009, Int. J. Biol. Macromol. 45(2): 169-73).

The availability of these bioactive compounds for commercial use is nevertheless tied to several restrictions:

1—limited availability of the plant material, since orchids are slow-growth plants and comprise numerous rare and protected species;

2—the presence of the above-described bioactive activities in the plant tissues of the orchids is subject to wide fluctuations tied to geographical origin, seasonal variability and contaminations of the cultivations by parasites;

3—the content of these compounds in plants is always quite low.

SUMMARY OF THE INVENTION

The inventors of the present invention have discovered that a valid alternative for obtaining high quantities of the previously-described bioactive compounds (hydrosoluble polysaccharides and phenylpropanoids) is to utilize stabilized and selected plant cell cultures.

The technology of plant cell cultures in fact allows overcoming the abovementioned problems.

One object of the invention is therefore a process (even industrial) for preparing meristematic cells with a high content of hydrosoluble polysaccharides and phenylpropanoids from cell cultures of plants belonging to the *Dendrobium, Phalaenopsis, Ansellia, Polyrrhiza, Vanilla, Cattleya* and *Vanda* genera and in particular to the following species: *Dendrobium polysema, Dendrobium farmeri, Dendrobium nobile, Phalaenopsis aphrodite, Phalaenopsis hybrida, Ansellia africana, Polyrrhiza lindenii, Vanilla planifolia, Cattleya labiata* and *Vanda coerulea*.

With the term "hydrosoluble polysaccharides" it is intended glucomannans, xyloglucans, arabinogalactans, hemicellulose and pectins based on D-galacturonic units.

In addition, in meristematic cells prepared from plants belonging to the *Dendrobium, Phalaenopsis, Ansellia, Polyrrhiza, Vanilla, Cattleya* and *Vanda* genera, a high extensin content was surprisingly prepared (extensins are glycoproteins rich in hydroxyproline which have a structure similar to collagen).

Another object of the present invention is therefore the preparation of meristematic cells with high extensin content.

It was seen that the meristematic cells obtained from the previously listed plant species have, as such, considerable antioxidant and anti-inflammatory activities, and activities of inhibition of the collagenase enzyme and the hyaluronidase enzyme.

Therefore, a further object of the invention is constituted by a preparation of meristematic cells obtained as described below, said preparation preferably being a glycerol suspension or solution, a lyophilized substance, a dried substance or a spray-dried preparation.

Other objects of the invention are such preparations of meristematic cells for use in cosmetic, nutritional and pharmaceutical applications.

Further objects and advantages of the present invention will be clearer from the following detailed description of the invention.

DETAILED DESCRIPTION OF THE INVENTION

The procedure for preparing even industrial quantities of plant meristematic cells with high content of phenylpropanoids, hydrosoluble polysaccharides and extensins comprises the following steps in succession:

1) selecting the clones deriving from the cell cultures of plants belonging to the *Dendrobium, Phalaenopsis, Ansellia Polyrrhiza, Vanilla, Cattleya* and *Vanda* genera in which maximized quantities of phenylpropanoids, hydrosoluble polysaccharides and extensins are present;

2) collecting the plant biomass deriving from a cell culture of said clones selected according to step 1) on liquid culture terrain;

3) separating the cells from the liquid culture terrain;

4) optionally, lyophilization and/or spray-drying of said cells or solution or suspension of said cells in glycerol.

Preferably, the step of collecting the biomass is achieved after cultivation in a fermenter of cells deriving from the plants of the above-listed species, comprising a first step of selecting the cell cultures based on the proliferation speed and on the content of phenylpropanoids, hydrosoluble polysaccharides and extensins.

In one embodiment, this procedure provides for the collection of tissue (preferably leaves, roots and pseudobulbs) from plants selected from one or more of the aforesaid genera, preferably from among the following species: *Dendrobium farmeri, Dendrobium polysema, Dendrobium nobile, Phalaenopsis aphrodite, Phalaenopsis hybrida, Ansellia africana, Polyrrhiza lindenii, Vanilla planifolia, Cattleya labiata* and *Vanda coerulea*, its cleaning, for example under running water, the minute fragmentation of 2-5 cm and sterilization on plates by means of sequential treatment with 70% ethanol for about 15', with 2% sodium hypochlorite for about 5 minutes and finally with 0.05% $HgCl_2$ for about 1 minute. Between one treatment and the next, the plant fragments are washed, typically three times or more, with sterile distilled water.

Each fragment, further chopped up (explants), of said tissue is deposited on Petri dishes containing nutritive terrain solidified due to the addition of Agar, with the addition of growth hormones and without antibiotics. The number of executed explants affects the outcome of the subsequent steps. Generally, 2000 to 5000 unpolluted explants are sufficient for proceeding with the subsequent selection step.

After a suitable time period, the undifferentiated callus tissue is formed, which is then multiplied after transfer onto a surface with greater area with fresh terrain.

Preferably, moreover, the plant cell line deriving from the undifferentiated callus tissue is stabilized by means of a certain number of transfers (subcultures) onto fresh culture terrain. In particular, it was observed that in order to obtain a stable cell line, it is important to operate at least ten subcultures. Such terrain is of solid type and can advantageously be constituted by 0.8-1% agar in a standard culture terrain to which vegetable peptone is added, which allows a balanced supply of amino acids and ensures the maintenance of good integrity of the cell wall.

Preferably, the vegetable peptone will be added in a quantity comprised between 500 and 4000 mg/L of culture terrain.

A "stable cell line" is defined as a culture which has the following characteristics:

high, constant proliferation speed over time;

preservation in the various subcultures of the same phenotype characteristics (color of the cells, friability of the aggregates, size etc.);

constant content, per unit of mass, of the phenylpropanoids, polysaccharides and extensins in the various subcultures (the content of phenylpropanoids, hydrosoluble polysaccharides and extensins is evaluated by means of chemical analysis of the extracts);

constant content, per unit of mass, of the primary metabolites (proteins, lipids and polysaccharides).

After the stabilization step, the cell line is subjected to a "clonal selection". Such selection consists of cultivating the stabilized cells for an appropriate time (typically 10-15 culture days). Subsequently, single aggregates of cells are collected from the solid culture terrain, and each of such cell aggregates are introduced onto the liquid culture terrain described above.

After a fermentation for a time such to obtain a suitable multiplication of the cell aggregate (from here on termed "clone"), generally comprised between 10 and 15 days, the content of the metabolite of interest is determined for each clone.

These operations can be repeated until a clone is selected of the plant cell line in which the productivity with regard to phenylpropanoids, polysaccharides and extensin is maximized.

It should be noted that the alternation of culture on solid and liquid terrain is essential for the purposes of the clonal selection process of the present invention. It is therefore essential that the clonal selection process described above does not conclude with the identification of the most active clone, but is constantly repeated in a manner so as to keep the selected clone with homogeneous phenotype.

The selected plant cell line is then multiplied to obtain a sufficient quantity of biomass for conducting the productive fermentation step. Such quantity will depend on the specific production needs, on the type of plant cell line employed and on the type of metabolite that one wishes to produce.

The biomass thus obtained can be passed directly into the final fermenter, or it can sustain one or more further growth steps in liquid terrain, operating with intermediate volumes.

Preferably, the above-exemplified procedure comprises the steps of:

a) cultivating, on solid terrain, a predetermined plant cell line stabilized for a time sufficient for obtaining the multiplication of said cell line to yield substantially separate cell groups;

b) collecting, from said solid terrain, said substantially separate cell groups and placing each of these in a separate liquid culture terrain;

c) cultivating each of said substantially separate cell groups in said liquid culture terrain for a sufficiently long time to allow the multiplication of said cell group and the analytical determination of the primary and/or secondary metabolites produced thereby;

d) operating a qualitative and quantitative determination of the primary and/or secondary metabolites produced by each of said cell groups in said liquid culture terrain;

e) selecting the cell group adapted to produce the greatest quantity of said metabolite of interest;

f) repeating the cycle of operations according to steps a), b), c), d) and e) on said cell group selected according to step e) for a sufficient number of times such that the quantity of said metabolite of interest produced by a selected cell group and by the cell group deriving from a subsequent cycle of selection operations is substantially unchanged.

In addition, the subsequent fermentation can preferably comprise the following steps:

A) introducing said plant clone in a liquid terrain, and multiplying it for a time sufficient to obtain an increase of the cell mass of at least 300% with respect to its weight;

B) optionally, transferring the suspension obtained in step A) on fresh liquid culture terrain and multiplying it for a time sufficient to obtain an increase of the cell mass of at least 300% with respect to its weight;

C) optionally, repeating step B) at least one more time;

D) transferring the suspension obtained in step A), B) or C) in a fresh liquid culture terrain in a fermenter to yield a biomass and conducting the fermentation in conditions and for a time such to obtain, in said biomass, a specific concentration of phenylpropanoids, hydrosoluble polysaccharides and extensins.

In accordance with a preferred embodiment, the fermentation will normally be operated at temperatures comprised between 15° C. and 35° C., typically about 25° C. and for a time normally comprised between 7 and 40 days, preferably between 14 and 21 days. It is essential that the biomass be suitably aerated and that at the same time it is subjected to agitation via agitation means outside the fermenter. It was in fact observed that plant biomass is composed of cells with walls that are poorly resistant to breakage. An agitator entering into the biomass mechanically acts on the cells and causes their lysis. Nevertheless, it is necessary that the agitation, while delicate, is efficient, above all in the final steps when the biomass density greatly increases. Agitation means particularly adapted for the purpose of the present invention are orbital agitation means. Such agitation means preferably operate at 40-200 rpm, more preferably at about 120 rpm.

It is opportune that the volume of the container (fermenter) in which the fermentation takes place is considerably greater than the volume of the biomass. Typically, the volume of the reactor will be from 50% to 200% greater than the volume of the biomass.

As stated above, an efficient conduction of the fermentation requires suitable oxygenation. The oxygenation is normally carried out with sterile air and with a flow of 0.5-4 L/minute, more preferably 2-2.5 L/minute, for a volume of 10 L of biomass. Alternatively, gaseous mixtures can be used contained from 10% to 100% v/v oxygen.

As stated above with regard to the agitation, even an overly strong bubbling oxidation can cause the breakage of the cell walls. Therefore, it is necessary to ensure that the oxygenation occurs in a delicate manner, e.g. by applying suitable diffusers to the bubbler. It will be preferable to use air or oxygen diffusion means with flow speed supplied at the nozzle outlet comprised between 10 m/min and 600 m/min, more preferably between 50 m/min and 350 m/min.

Even the shape of the fermentation chamber has considerable importance. It is recommended that it have a smooth and uniform surface, i.e. that it does not contain edges, corners or other parts that can cause the breakage of biomass cell walls.

According to a particular embodiment of the present invention, additives will be added to the biomass in order to increase the solubility of the oxygen in the water. Such additives will preferably be selected from among those substances defined as "artificial blood", e.g. perfluorinated hydrocarbons (PFC).

In particular, for the object of the present invention, stabilized cell lines derived from plant tissue of plants of the aforesaid genera and preferably of *Dendrobium farmeri, Dendrobium polysema, Dendrobium nobile, Phalaenopsis aphrodite, Phalaenopsis hybrida, Ansellia africana, Polyrrhiza lindenii, Vanilla planifolia, Cattleya labiata* and *Vanda coerulea* were selected for their capacity to produce:

phenylpropanoids in quantities greater than 0.1% (expressed on dry cell weight), preferably greater than 1%, more preferably greater than 10% of the dry cell weight.

hydrosoluble polysaccharides in quantities greater than 5% (expressed on dry cell weight), preferably greater than 10%, more preferably greater than 20%.

extensin in quantities greater than 0.01% (expressed on dry cell weight), preferably greater than 0.05%, more preferably greater than 0.1%.

Process of Preparation of the "Stems" (Meristematic Cells)

The process of preparation of the meristematic cells from the previously listed cell lines provides for the following steps in succession:

1. selecting the clone deriving from the cell culture of plant cells belonging to the previously listed genera, in which the greatest concentration of phenylpropanoids, hydrosoluble polysaccharides and extensins is present;

2. collecting the plant biomass deriving from a cell culture of said selected clones, in liquid terrain;

3. separating the cells from the liquid culture terrain;

4. optionally, lyophilization or spray-drying of the cells or solution or suspension of the cells in glycerol, or in glycerol added with xanthan gum (in a quantity variable from 0.1 to 2% W/W, preferably in a quantity equal to 0.3%) or in butylene glycol.

A. Preparation of the Glycerol "Stems"

In particular, cell cultures of the cell lines of *Dendrobium farmeri, Dendrobium polysema, Dendrobium nobile, Phalaenopsis aphrodite, Phalaenopsis hybrida, Ansellia africana, Polyrrhiza lindenii, Vanilla planifolia, Cattleya labiata* and *Vanda coerulea*, stabilized and selected as stated above, are collected at an age comprised between 7 and 21 days. The cells are preliminarily separated from the culture terrain by means of filtration due to gravity, pressure filtration or centrifugation over a porous net, e.g. nylon net, steel net, cotton net, etc., preferably having porosity comprised between 50 μm and 150 μm. The meristematic cells separated from the culture terrain are suspended in glycerol in a weight/volume ration equal to 20:80 (concentration interval 5:95-50:50). The preparations thus obtained represent the glycerol stems.

B. Preparation of Lyophilized "Stems"

In accordance with a first embodiment variant of the procedure, suspended cell cultures of the stabilized and selected lines of *Dendrobium farmeri, Dendrobium polysema, Dendrobium nobile, Phalaenopsis aphrodite, Phalaenopsis hybrida, Ansellia africana, Polyrrhiza lindenii, Vanilla planifolia, Cattleya labiata* and *Vanda coerulea*, always collected at an age comprised between 7 and 21 days, are preliminarily separated from the culture terrain by means of filtration due to gravity, pressure filtration or centrifugation over a porous net, e.g. nylon net, steel net, cotton net, etc., preferably having porosity comprised between 50 μm and 150 μm. The obtained cells are subjected to lyophilization according to conventional techniques. The lyophils obtained represent the lyophilized stems.

C. Preparation of Spray-Dried "Stems"

According to a further embodiment of the invention, suspended cell cultures of the previously described cell lines, collected at an age comprised between 7 and 21 days and filtered according to a general scheme described in B, are subjected to a spray-drying process according to conventional techniques. The powders obtained represent the spray-dried stems.

The "spray-drying" technique is a known technique and is widely used in food and pharmaceutical fields. It provides for the atomization of the liquid (in the present case an aqueous solution of meristematic cells) through suitable nozzles in a chamber, where the atomized liquid is hit (in co-current or counter-current) by a hot gas (air or nitrogen). In this manner, the water of the suspension instantly evaporates and the cells form a powder with controlled grain size (also due to the type of atomized nozzle used). The equipment for the spray-drying is of commercial type.

D. Preparation of Dried "Stems"

According to a further embodiment of the invention, suspended cell cultures of the previously described cell lines, collected at an age comprised between 7 and 21 days and filtered according to a general scheme described in B, are subjected to a drying process according to conventional techniques. The obtained powders represent the dried stems.

The drying of the filtered cells is carried out in a ventilated oven at a temperature between 40° C. and 70° C. for a time period comprised between 12 hours and 72 hours.

As a non-limiting example, the preparation procedures are reported of the lyophilized and spray-dried glycerol stems obtained from stabilized cell cultures and selected for the high content of phenylpropanoids, hydrosoluble polysaccharides and extensins.

Example 1

Preparation of the Glycerol Stems of *Dendrobium Farmeri*

Cells that were stabilized and selected as described above, deriving from the line of *Dendrobium farmeri*, grown on solid terrain (Gamborg B5 containing 1% (W/V) Agar, 20 g/L sucrose, 0.5 g/L vegetable peptone, 2 mg/L NAA and 1 mg/L Kinetin, final pH equal to 6.5) were introduced into 5 flasks with 3-liter capacity, containing 1000 ml of liquid terrain (Gamborg B5 containing 20 g/L sucrose, 0.5 g/L vegetable peptone, 2 mg/L NAA and 1 mg/L Kinetin, final pH finale equal to 6.5). The quantity of plant cells introduced into liquid terrain was equal to 5% W/V. The suspensions thus obtained were incubated at 25° C., in darkness and placed on top of an orbital agitator regulated at 120 RPM. After 14 days of incubation, the plant biomass (5 liters of cell suspension) was collected and filtered over nylon nets with 50 µm porosity. From 5 liters of cell suspension, cells with 400 g wet weight were obtained, equal to 20.7 g dry weight, with a content of phenylpropanoids equal to 3.3 g, with a content of hydrosoluble polysaccharides equal to 4.6 g and with an extensin content equal to 0.08 g. The collected cells were suspended in glycerol in a weight volume ratio equal to 20:80. The obtained preparation represents the glycerol stems of *Dendrobium farmeri* (DfSG).

Example 2

Preparation of the Lyophilic Stems of *Phalaenopsis Aphrodite*

Cells that were stabilized and selected as described above, deriving from the line of *Phalaenopsis aphrodite*, grown on solid terrain (Gamborg B5 containing 1% (W/V) Agar, 20 g/L sucrose, 0.5 g/L vegetable peptone, 3 mg/L NAA and 0.5 mg/L Kinetin, final pH equal to 6.5) were introduced into 5 flasks with 3-liter capacity, containing 1000 ml of liquid terrain (Gamborg B5 containing 20 g/L sucrose, 0.5 g/L vegetable peptone, 3 mg/L NAA and 0.5 mg/L Kinetin, final pH finale equal to 6.5). The quantity of plant cells introduced into the liquid terrain was equal to 7% W/V. The suspensions thus obtained were incubated at 25° C., in darkness and placed on top of an orbital agitator regulated at 120 RPM. After 14 days of incubation, the plant biomass (5 liters of cell suspension) was collected and filtered over nylon nets with 50 µm porosity. The collected cells were subjected to lyophilization. From 5 liters of cell suspension, 25 g of lyophilized cells were obtained with a content of phenylpropanoids equal to 4.7 g, with a content of hydrosoluble polysaccharides equal to 5.75 g and with an extensin content equal to 0.08 g. The preparation obtained represents the lyophilized steps of *Phalaenopsis aphrodite* (PaSL).

Example 3

Preparation of the Lyophilic Stems of *Ansellia Africana*

Cells that were stabilized and selected as described above, deriving from the line of *Ansellia africana*, grown on solid terrain (Gamborg B5 containing 1% (W/V) Agar, 20 g/L sucrose, 2 g/L vegetable peptone, 2 mg/L NAA and 1 mg/L Kinetin, final pH equal to 6.5) were inoculated in 5 flasks with 3-liter capacity, containing 1000 ml of liquid terrain (Gamborg B5 containing 20 g/L sucrose, 2 g/L vegetable peptone, 2 mg/L NAA, and 1 mg/L Kinetin, final pH equal to 6.5). The quantity of plant cells inoculated into the liquid terrain was equal to 7.5% W/V. The suspensions thus obtained were incubated at 25° C., in darkness and placed on top of an orbital agitator regulated at 120 RPM. After 14 days of incubation, the plant biomass (5 liters of cell suspension) was collected and filtered over nylon nets with 50 µm porosity. The collected cells were subjected to lyophilization. From 5 liters of cell suspension, 18 g of lyophilized cells were obtained with a content of phenylpropanoids equal to 3.25 g, with a content of hydrosoluble polysaccharides equal to 4.12 g and with an extensin content equal to 0.05 g. The obtained preparation represents the lyophilized stems of *ansellia africana* (AaSL).

Example 4

Preparation of the Lyophilic Stems of *Polyrrhiza Lindenii*

Cells that were stabilized and selected as described above, deriving from the line of *Polyrrhiza lindenii*, grown on solid terrain (Gamborg B5 containing 1% (W/V) Agar, 10 g/L sucrose, 1 g/L vegetable peptone, 3 mg/L NAA and 0.3 mg/L Kinetin, final pH equal to 6.5) were inoculated in 5 flasks with 3-liter capacity, containing 1000 ml of liquid terrain (Gamborg B5 containing 10 g/L sucrose, 1 g/L vegetable peptone, 3 mg/L NAA, and 0.3 mg/L Kinetin, final pH equal to 6.5). The quantity of plant cells inoculated into the liquid terrain was equal to 8% W/V. The suspensions thus obtained were incubated at 25° C., in darkness and placed on top of an orbital agitator regulated at 120 RPM. After 14 days of incubation, the plant biomass (5 liters of cell suspension) was collected and filtered over nylon nets with 50 µm porosity. The collected cells were subjected to lyophilization. From 5 liters of cell suspension, 15 g of lyophilized cells were obtained with a content of phenylpropanoids equal to 2.81 g, with a content of hydrosoluble polysaccharides equal to 3.25 g and with an extensin content equal to 0.03 g. The obtained preparation represents the lyophilized stems of *polyrrhiza lindenii* (PlSL).

Example 5

Preparation of the Lyophilic Stems of *Vanilla Planifolia*

Cells that were stabilized and selected as described above, deriving from the line of *Vanilla planifolia*, grown on solid terrain (Gamborg B5 containing 1% (W/V) Agar, 20 g/L sucrose, 2 g/L vegetable peptone, 1 mg/L NAA, 0.5 mg/L IAA and 2 mg/L Kinetin, final pH equal to 6.5) were inoculated in 5 flasks with 3-liter capacity, containing 1000 ml of liquid terrain (Gamborg B5 containing 20 g/L sucrose, 2 g/L vegetable peptone, 1 mg/L NAA, 0.5 mg/L IAA and 2 mg/L Kinetin, final pH equal to 6.5). The quantity of plant cells inoculated into the liquid terrain was equal to 5% W/V. The suspensions thus obtained were incubated at 25° C., in darkness and placed on top of an orbital agitator regulated at 120 RPM. After 14 days of incubation, the plant biomass (5 liters of cell suspension) was collected and filtered over nylon nets with 50 µm porosity. The collected cells were subjected to lyophilization. From 5 liters of cell suspension, 28 g of lyophilized cells were obtained with a content of phenylpropanoids equal to 5.12 g, with a content of hydrosoluble polysaccharides equal to 6.35 g and with an extensin content equal to 0.09 g. The obtained preparation represents the lyophilized stems of *vanilla planifolia* (VpSL).

Example 6

Preparation of the Lyophilic Stems of *Cattleya Labiata*

Cells that were stabilized and selected as described above, deriving from the line of *Cattleya labiata*, grown on solid terrain (Gamborg B5 containing 1% (W/V) Agar, 25 g/L sucrose, 2 g/L vegetable peptone, 3 mg/L NAA, and 1 mg/L Kinetin, final pH equal to 6.5) were inoculated in 5 flasks with 3-liter capacity, containing 1000 ml of liquid terrain (Gamborg B5 containing 25 g/L sucrose, 2 g/L vegetable peptone, 3 mg/L NAA, and 1 mg/L Kinetin, final pH equal to 6.5). The quantity of plant cells inoculated into the liquid terrain was equal to 6% W/V. The suspensions thus obtained were incubated at 25° C., in darkness and placed on top of an orbital agitator regulated at 120 RPM. After 14 days of incubation, the plant biomass (5 liters of cell suspension) was collected and filtered over nylon nets with 50 µm porosity. The collected cells were subjected to lyophilization. From 5 liters of cell suspension, 22 g of lyophilized cells were obtained with a content of phenylpropanoids equal to 4.18 g, with a content of hydrosoluble polysaccharides equal to 5.05 g and with an extensin content equal to 0.06 g. The obtained preparation represents the lyophilized stems of *cattleya labiata* (ClSL).

Example 7

Preparation of the Spray-Dried Stems of *Dendrobium Polysema*

Cells that were stabilized and selected as described above, deriving from the line of *Dendrobium polysema*, grown on solid terrain (Gamborg B5 containing 1% (W/V) Agar, 20 g/L sucrose, 0.5 g/L vegetable peptone, 2 mg/L NAA, 0.5 mg/L IAA, and 1 mg/L Kinetin, final pH equal to 6.5) were inoculated in 5 flasks with 3-liter capacity, containing 1000 ml of liquid terrain (Gamborg B5 containing 30 g/L sucrose, 2 g/L vegetable peptone, 2 mg/L NAA, 0.5 mg/L IAA, and 1 mg/L Kinetin, final pH equal to 6.5). The quantity of plant cells inoculated into the liquid terrain was equal to 6% W/V. The suspensions thus obtained were incubated at 25° C., in darkness and placed on top of an orbital agitator regulated at 120 RPM. After 14 days of incubation, the plant biomass (5 liters of cell suspension) was collected and filtered over nylon nets with 50 µm porosity. The collected cells were subjected to spray-drying. From 5 liters of cell suspension, 29 g of spry-dried cells were obtained with a content of phenylpropanoids equal to 6.2 g, with a content of hydrosoluble polysaccharides equal to 8.1 g and with an extensin content equal to 0.1 g. The obtained preparation represents the spry-dried stems of *dendrobium polysema* (DpSD).

Example 8

Preparation of the Spray-Dried Stems of *Vanda Coerulea*

Cells that were stabilized and selected as described above, deriving from the line of *Vanda coerulea*, grown on solid terrain (Gamborg B5 containing 1% (W/V) Agar, 10 g/L sucrose, 0.5 g/L vegetable peptone, 3 mg/L NAA and 1 mg/L Kinetin, final pH equal to 6.5) were inoculated in 5 flasks with 3-liter capacity, containing 1000 ml of liquid terrain (Gamborg B5 containing 10 g/L sucrose, 0.5 g/L vegetable peptone, 3 mg/L NAA and 1 mg/L Kinetin, final pH equal to 6.5). The quantity of plant cells inoculated into the liquid terrain was equal to 7% W/V. The suspensions thus obtained were incubated at 25° C., in darkness and placed on top of an orbital agitator regulated at 120 RPM. After 14 days of incubation, the plant biomass (5 liters of cell suspension) was collected and filtered over nylon nets with 50 µm porosity. The collected cells were subjected to spray-drying. From 5 liters of cell suspension, 19 g of spray-dried cells were obtained with a content of phenylpropanoids equal to 3.5 g, with a content of hydrosoluble polysaccharides equal to 4.37 g and with an extensin content equal to 0.07 g. The obtained preparation represents the spray-dried stems of *vanda coerulea* (VcSD).

Example 9

Determination of the Phenylpropanoid Content in the Cell Cultures of *Dendrobium, Phalaenopsis, Ansellia, Polyrrhiza, Vanilla, Cattleya* and *Vanda* Selected for the Preparation of Stems The determination of the phenylpropanoid content in the selected cell cultures of *Dendrobium, Phalaenopsis, Ansellia, Polyrrhiza, Vanilla, Cattleya* and *Vanda* for the preparation of stems was carried out by collecting 10 mL of the cell suspension to be examined. An equal volume of methanol is added to the collected sample, as is 5 mg/mL of ascorbic acid. The obtained suspension is subjected to homogenization in Ultraturrax.

After the homogenization treatment, the suspension is filtered over 0.45 µm Millipore filter, or centrifuged. A part of the clear solution is injected, after suitable dilution, in HPLC for qualitative-quantitative analysis. In this manner, information is obtained on the production of phenylpropanoids per unit of volume (µg/mL of culture).

In order to obtain the specific production information (μg/g fresh cells), a known quantity of culture is collected, filtered over Buchner funnel and the separated cells are weighed, then suspended in methanol; ascorbic acid is added and then the mixture is subjected to homogenization with Ultraturrax as described above. Analogously, the suspension is filtered or centrifuged and analyzed in HPLC. For the quantitative determination of the components of the mixture, reverse phase HPLC is used. The detection of the analytes occurs through equal absorbance measurements at 330 nm, absorbance maximum of the caffeic acid. The HPLC analyses were carried out by using an Agilent mod. 1100 liquid chromatograph equipped with photodiode detector.

The employed method is described below:
Phenomenex Luna Column $C_{18}$ 4.6×150 mm, thermostated at 30° C.
Solvent A: 0.01N $H_3PO_4$ in $H_2O$
Solvent B: 0.01N $H_3PO_4$ in $CH_3CN$
Flow: 0.8 mL/min
Detection at 330 nm
Gradient elution as follows:

| time | % B |
|------|-----|
| 0    | 0   |
| 10   | 10  |
| 15   | 20  |
| 20   | 25  |
| 25   | 35  |
| 30   | 45  |
| 35   | 55  |
| 40   | 0   |

The single peaks were quantified by expressing them in caffeic acid.

Example 10

Determination of the Content of Hydrosoluble Polysaccharides in the Cell Cultures of *Dendrobium, Phalaenopsis, Ansellia, Polyrrhiza, Vanilla, Cattleya* and *Vanda* Selected for the Preparation of Stems In plant cells, hydrosoluble polysaccharides are essential constituents of the wall and extra-cellular matrix. These components carry out various functions including defining the cell shape, providing a rigid barrier for volume fluctuations following osmotic variations, functions of accumulation and conservation of water in tissues such as roots, pseudobulbs, leaves and flowers, in addition to representing energy sources (Wang C Y et al. 2008, Planta, 227(5):1063-1077). In order to carry out all the biological functions, there are various forms of polysaccharides, such as insoluble celluloses, which confer rigidity to the wall. The celluloses are linear polymers of glucose molecules covalently bonded with β(1-4) Bond. Other forms of polysaccharides are represented by polymers constituted by multiple monosaccharide components in which mannose prevails over glucose in a 3:1 molar ratio; these are called glucomannans. Also these polymers have a non-branched structure (Daloul M, et al. 1963, Bulletin de la Societe de Chimie Biologique). These polysaccharides are more soluble in water (Shcherbukhina N K, et al. 1969, Inst. Biokhim. im. Bakha, Moscow, USSR. Rastitel'nye Resursy) and are therefore more easily extractable from plants. The polysaccharide content in the plants varies widely among the various species, among the different tissues of each plant, and, in the scope of each tissue, varies with the age of the plant (Lu H, et al. 2007, Zhongshan Daxue Xuebao, Ziran Kexueban, 46(3), 79-83. Publisher: Zhongshan Daxue Xuebao Bianjibu). Such variability sets serious problems with regard to the standardization of the extracted material, complicating the application for the production on industrial scale. In the cell wall, finally, there are water-soluble branched polysaccharides such as xyloglucans, arabinogalactans, hemicellulose and pectins based on D-galacturonic units.

Polysaccharides are also produced from orchid cell cultures (Song J, et al. 2008, Yunnan Zhiwu Yanjiu, 30(1), 105-109) which can thus represent a useful alternative source for the extraction of substances from rare plants, allowing greater extract standardization.

The water-soluble polysaccharides extractable from the plant are useful for cosmetic applications. Hydrosoluble polysaccharides extracted from orchids of the Odontoglossum family have shown considerable effectiveness in reducing the lipoperoxidation of the skin, in determining the increase of the hydration levels and synthesis of collagen IV in the dermis (Sasaki A, et al. 2009 PCT Int. Appl. WO 2009139231 A1).

The determination of the polysaccharide content in the selected cell cultures of *Dendrobium, Phalaenopsis, Ansellia, Polyrrhiza, Vanilla, Cattleya* and *Vanda* was carried out by collecting a previously homogenized cell suspension portion. The homogenization was carried out by means of suitable systems such as: high speed mixers or high pressure cell disintegrators such as French-pumps. The extraction of the polysaccharides can be directly actuated on the homogenized product or on a spent pellet, obtained from a preceding activity of extraction with organic solvent mixtures and water (e.g. ethanol/water or acetone water) employed in order to previously extract other fractions of organic compounds of interest, such as polyphenols, flavonoids, alkaloids or other compounds.

The homogenized compound is hot treated with 2-5 volumes of water at 80-90° C. for 30 min, controlling the pH at values comprised between 6.0 and 7.5. The supernatant is separated from the pellet via centrifugation and the pellet is once again extracted with 2 volumes of hot water. The aqueous extract is then subjected to ultrafiltration with low-polysaccharide-retention membranes and suitable cut-off. A first filtration is carried out over 1,000,000 Da cut-off in order to separate not-perfectly-soluble mucilaginous components in the retention area; a second filtration is also carried out at 3000-5000 Da in order to concentrate the solution. The polysaccharide is recovered in solid form via precipitation with 2 volumes of acetone and is subsequently dried via lyophilization and finally quantitatively weighed.

Example 11

Determination of the Extensin Content in the Cell Cultures of *Dendrobium, Phalaenopsis, Ansellia, Polyrrhiza, Vanilla, Cattleya* and *Vanda* Selected for the Preparation of Stems The analysis of the proteins which compose the cell wall emphasized the role carried out by the family of glycoproteins rich in hydroxyproline (HRGP), as main components. In the HRGP group, the lectins rich in hydroxyproline and the extensins were further underlined. The extensin amino acid sequence is highly repetitive and contains a characteristic pentapeptide motif (Ser-Pro-Pro-Pro-Pro) in which the residues of proline (Pro) are first hydroxylated, becoming a pentapeptide with hydroxyproline (Ser-Hyp-Hyp-Hyp-Hyp) and then glycolsylated, and in some cases the glycosylation reaches about 50% of the molecule weight. There are various forms of extensin, which differ by the amino acid sequence that is interposed between two adjacent Ser-(Hyp)$_4$ motifs in which one or more tyrosines are present. It is also well known that extensins are particularly difficult to extract from the cell wall. Indeed, extensins are initially synthesized as soluble monomers with molecular weight between 60,000 Dalton and 90,000 Dalton, which subsequently become insoluble in the plant cell wall by means of intra- and intermolecular bridges formed by covalent bonds between tyrosine residues present on adjacent monomers. Such rigid and insoluble structure, together with polysaccharides such as cellulose, ensures the solidity and mechanical tension necessary for maintaining the form of the plant cell. A method for extracting extensins from plants thus requires a hydrolytic treatment with various chemical agents in order to produce a hydrolysate of extensins constituted by small glycosylated fragments of extensins.

The extensins present numerous aspects of cosmetic interest due to a content of Pro and Hyp comparable to that of animal collagen. Indeed, some cosmetic applications report the use of extensin hydrolysates as "plant collagen" (PARK H J, Ptn. Appl. KR 20070117355 A; Wolf B, EP 0533408 B2).

Nevertheless, the molecular weight of the extensin hydrolysates is situated between 100-1500 Dalton, while the weight of a monomer extensin protein is greater than 60,000 Dalton.

From plant cell cultures undergoing rapid growth, it is possible to extract a high quantity of monomer extensin.

The determination of the extensin content in the selected cell cultures of *Dendrobium, Phalaenopsis, Ansellia, Polyrrhiza, Vanilla, Cattleya* and *Vanda* regards the bioavailable soluble form which is extracted from the cell wall with a buffer with high ionic force. The extraction was carried out by collecting 1 liter of cells in exponential growth phase according to the following protocol:

1) Vacuum filtering the cell culture over Buchner funnel with 50 um mesh and eliminating the culture terrain;
2) Quickly washing the cells, resuspending them in 1 L osmotic water;
3) Newly filtering and eliminating the liquid;
4) Resuspending the cells in 200 mL extraction buffer (solution A: 200 mM NaCl, 1 g/L Ascorbic Acid and bringing to pH 3.0 with 6M HCl;
5) Maintaining the culture under agitation for 5 minutes, then filtering and retaining the filtrate;
6) Adding, to the filtrate, Trichloroacetic acid (TCA) to a final concentration of 10%. Incubating at 4° C. for 12 h.

In this manner, most of the proteins present in the extract precipitate. On the other hand, the extensins, since they are highly glycosylated and have basic nature, remain in solution;
7) Centrifuging the solution at 8,000 rpm for 20 minutes at 4° C.;
8) Collecting the supernatant and dialyzing the solution in an excess of water for 24 h;
9) Lyophilizing the dialyzed sample;
10) Resuspending, in the solution B (30 mM Sodium-Phosphate Buffer, pH 7.8) and metering the hydroxyproline (according to Kivirikko, K. I., 1967 Anal Biochem. 19(2): 249-55) by means of acid hydrolysis followed by pyrrole oxidation and coloration with the Ehrlich reactive. Hydroxyproline represents 40% of the weight of the extensins.

The preparations obtained according to the procedure described in examples 1, 2, 3, 4, 5, 6, 7 and 8 were used to prepare several biological assays. Hereinbelow, several examples are reported, given as indicative but non-limiting of the antioxidant activity, anti-inflammatory activity, inhibition of the collagenase and inhibition of the hyaluronidase of the preparations of meristematic cells, object of the invention.

Example 12

Determination of the Antioxidant Activity of the Glycerol Stems of *Dendrobium Farmeri*

The determination of the antioxidant activity of the glycerol stems of the line of *Dendrobium farmeri* (prepared as described in example 1) was carried out by means of the use of the free radical DPPH. 500 µL of a 100 µM solution of DPPH were incubated for 15 minutes at room temperature with an equal volume of glycerol stems of *Dendrobium farmeri*. During incubation, the DPPH is reduced, losing the characteristic violet color in favor of a pale yellow color. The value of the absorbance was measured by a spectrophotometer at a wavelength of 515 nm.

The antiradical activity is expressed as a concentration of the antioxidant agent, which lowers by 50% the concentration of the initial DPPH ($IC_{50}$).

Figure 1:
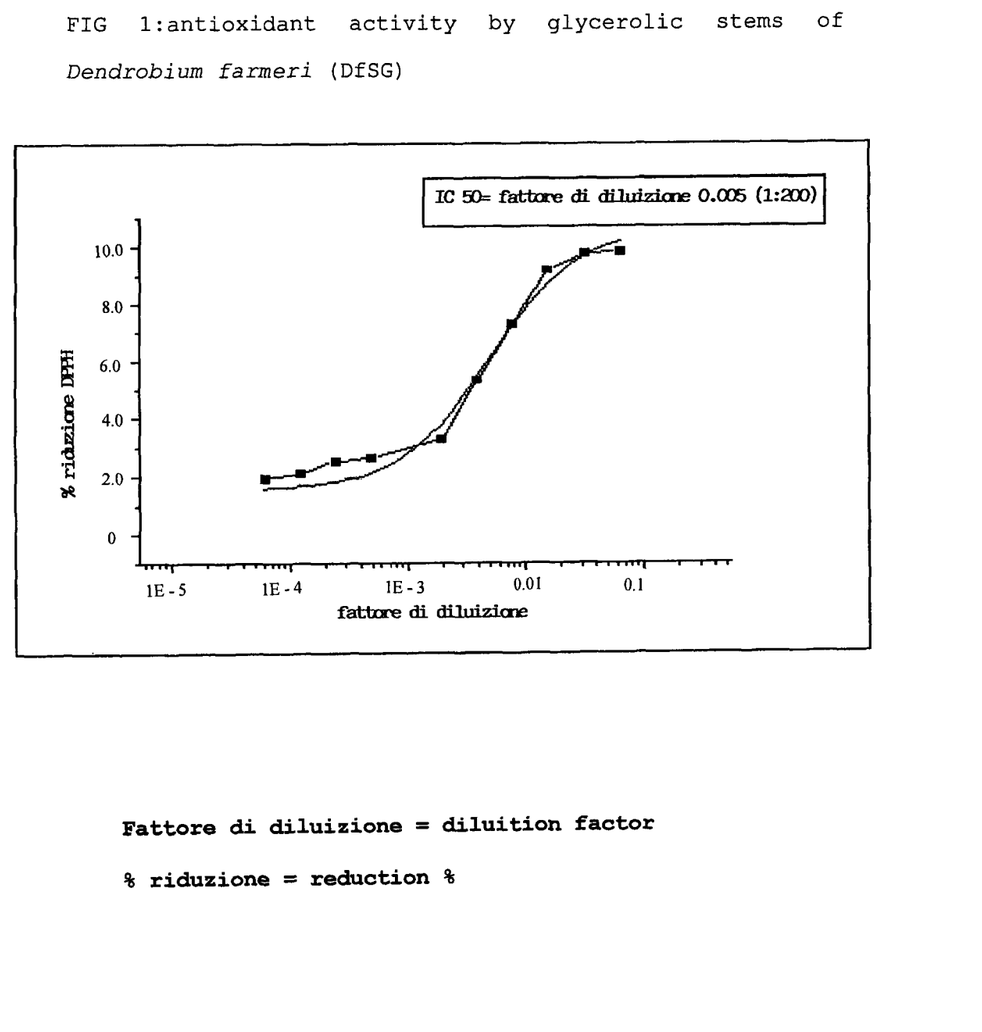
FIG. 1: antioxidant activity by meristematic cells of *Dendrobium farmeri* (DfSG) in glycerol solution.

The value of $IC_{50}$ obtained by assaying the preparation of glycerol stems of *Dendrobium farmeri* (DfSG) is the following (see graph of FIG. 1):

$IC_{50}$=1:200 Dilution of glycerol stems DfSG

Example 13

Determination of the Activity of Inhibition of the Hyalyronidase Enzyme by the Lyophilized Stems of *Phalaenopsis Aphrodite, Ansellia Africana* and *Polyrrhiza Lindenii*

The capacity of lyophilized stems of *Phalaenopsis Aphrodite, Ansellia Africana* and *Polyrrhiza lindenii* (prepared as described in examples 2, 3 and 4) to inhibit the degradation of the hyaluronic acid present in the extracellular matrix was evaluated by means of the test of inhibition of the activity of the hyaluronidase enzyme.

The test provides for a first incubation of the sample to be analyzed in the presence of 50 U of the hyaluronidase enzyme for 15 minutes at 37° C., at the end of which there follows a second incubation for 45 minutes at 37° C. after the addition of a hyaluronic acid solution at 3 mg/mL.

The samples were brought to boiling for 3 minutes, cooled quickly in ice and added to 3 mL of a 10 mg/mL DMAB solution.

The solution was incubated at 37° C. for 20 minutes and the value of the absorbance was determined by spectrophotometer at the wavelength of 544 nm.

The results obtained by assaying the sample of *Phalaenopsis aphrodite, Ansellia Africana* and *Polyrrhiza lindenii* are reported in Tables 1, 2 and 3.

TABLE 1

Activity of inhibition of the hyaluronidase enzyme by the lyophilized stems of *Phalaenopsis aphrodite* (PaSL)

| Sample | % inhibition |
| --- | --- |
| 50 µg/mL PaSL | 0.72 |
| 100 µg/mL PaSL | 12.5 |
| 200 µg/mL PaSL | 41.8 |
| 400 µg/mL PaSL | 66.4 |
| 800 µg/mL PaSL | 87.5 |

TABLE 2

Activity of inhibition of the hyaluronidase
enzyme by the lyophilized stems of *Anisellia Africana*
(AaSL)

| Sample | % inhibition |
| --- | --- |
| 50 µg/mL AaSL | 3.84 |
| 100 µg/mL AaSL | 25.5 |
| 200 µg/mL AaSL | 64.3 |
| 400 µg/mL AaSL | 81.1 |
| 800 µg/mL AaSL | 90.8 |

TABLE 3

Activity of inhibition of the hyaluronidase
enzyme by the lyophilized stems of *Polyrrhiza lindenii*
(PlSL)

| Sample | % inhibition |
| --- | --- |
| 50 µg/mL PlSL | 1.93 |
| 100 µg/mL PlSL | 18.6 |
| 200 µg/mL PlSL | 47.1 |
| 400 µg/mL PlSL | 76.6 |
| 800 µg/mL PlSL | 92.1 |

Example 14

Determination of the Anti-Inflammatory Activity of the Spray-Dried Stems of *Dendrobium Polysema, Vanda Coerulea* and the Lyophilic Stems of *Vanilla Planifolia*

The determination of the anti-inflammatory activity of spray-dried stems of *Dendrobium polysema* (prepared as described in example 7) and *Vanda coerulea* (prepared as described in example 8) and the lyophilic stems of *Vanilla planifolia* (prepared as described in example 5) was evaluated by means of a biological test which uses the cell line of mice macrophages RAW 264.7. The test was prepared by means of introducing the cells of the RAW 264.7 line into 96-well plates in DMEM+10% FCS culture terrain. Upon reaching 80% cell confluence, the culture terrain was substituted with conditioned terrain with the compound to be tested, with and without a 20 µg/mL LPS solution, and left in incubation for 24 h at 37° C. in humidified atmosphere with 5% $CO_2$. At the end of incubation, 90 µL of supernatant of the culture were left for 10 minutes at ambient temperature with 10 µL of Griess Reagent. The absorbance of the solution was measured by spectrophotometer at 540 nm and the nitric oxide concentration (NO) present in the samples was extrapolated from a standard curve of $NaNO_2$.

Figure 2:
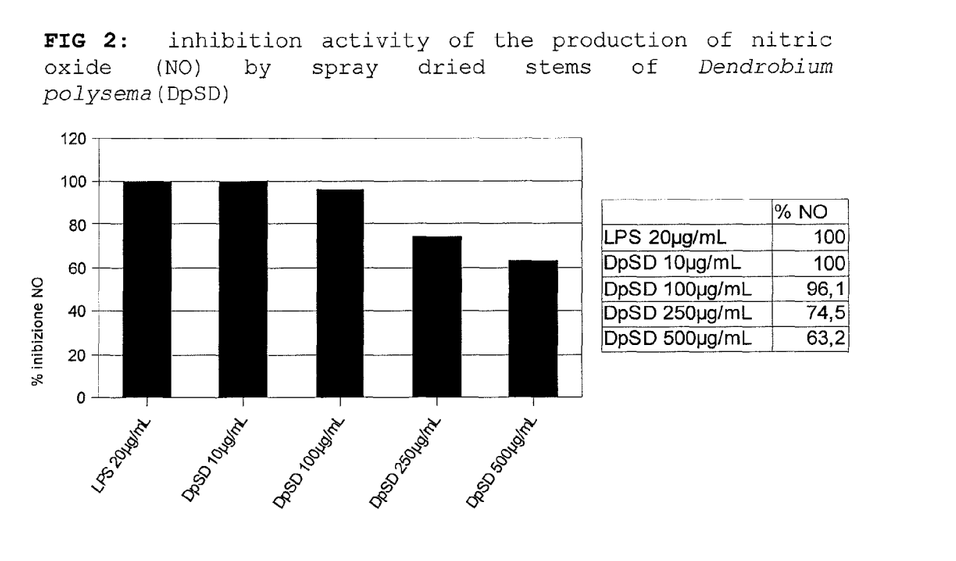
FIG. 2: activity of inhibition of the NO production by spray-dried meristematic cells of *Dendrobium polysema* (DpSSD)
Figure 3:
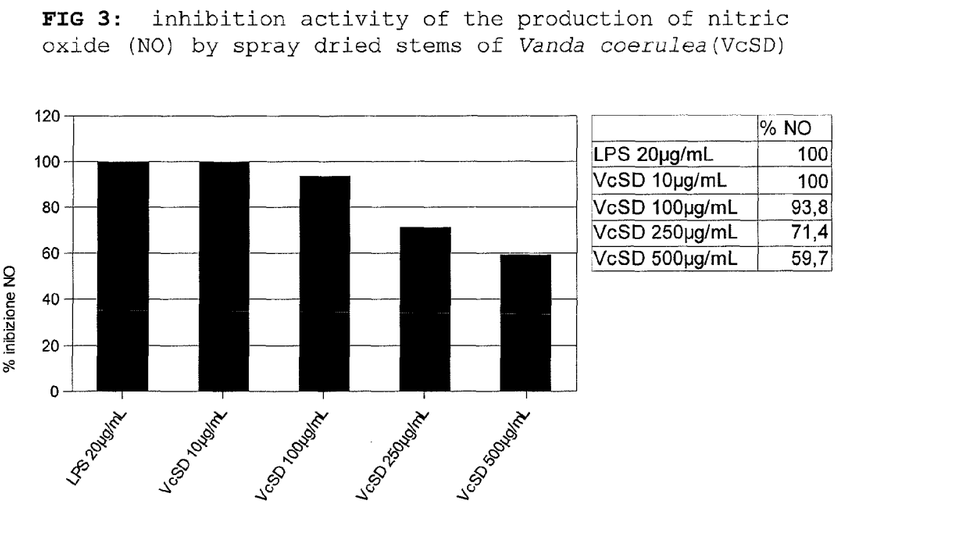
FIG. 3: activity of inhibition of the NO production by lyophilized meristematic cells of *Vanilla planifolia* (VpSL)
Figure 4:
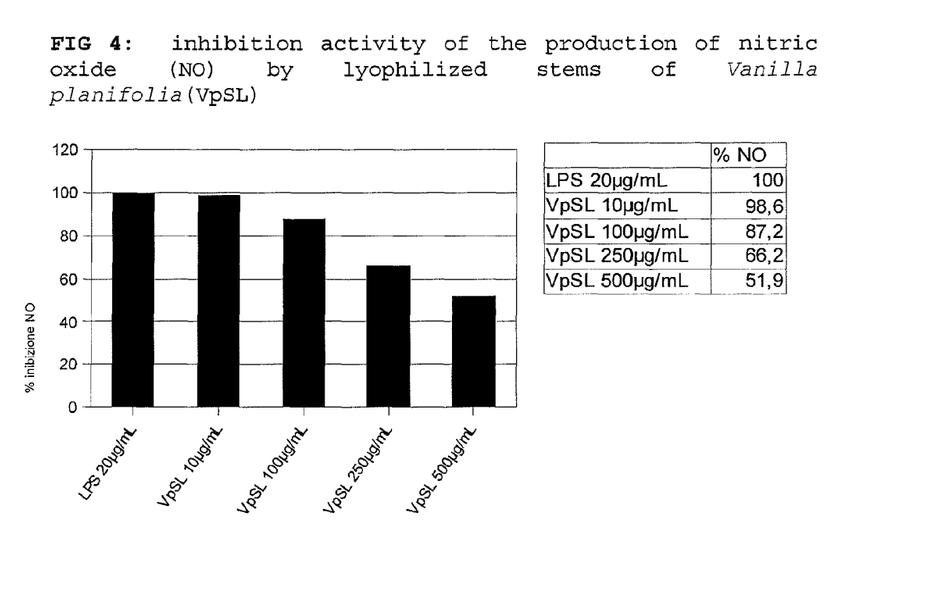
FIG. 4: activity of inhibition of the NO production by lyophilized meristematic cells of *Vanda Coerulea* (VcSL)

The results obtained by assaying the spray-dried stems of *Dendrobium polysema* (DPSSD), *Vanda coerulea* (VcSD) and *Vanilla planifolia* (VpSl) are reported in FIG. 2, FIG. 3 and FIG. 4.

Example 15

Determination of the Activity of Inhibition of Collagenase by Lyophilized Stems of *Dendrobium Nobile* and *Cattleya Labiata*

The determination of the activity of lyophilized stems of *Dendrobium nobile* and *Cattleya labiata* in inhibiting the degradation of the collagen of the extracellular matrix via the inhibition of the collagenase enzyme was evaluated by means of the spectrophotometric dosage of hydroxyproline. The test provides for the gelification in 6-well plate of 500 µL collagen and the subsequent incubation for 15 h at 37° C. of the sample of stems, with and without 70 U/mL collagenase enzyme. Once the incubation period has ended, the samples are washed with 1×PBS, dried in nitrogen gas and subjected to acid hydrolysis with 6M HCl for 15-18 h at 110° C. After having dried them once again in nitrogen gas and resuspended in acetate/citrate buffer, 100 µL of sample is incubated at ambient temperature and away from light for 25 minutes with 100 µL of a 7% chloramine solution. A second incubation for 15 minutes at 60° C. is executed after the addition of 100 µL of Ehrlich solution, at the end of which a spectrophotometric reading is made at 540-560 nm and the quantity of hydroxyproline present in the samples is extrapolated from a standard curve.

Figure 5:
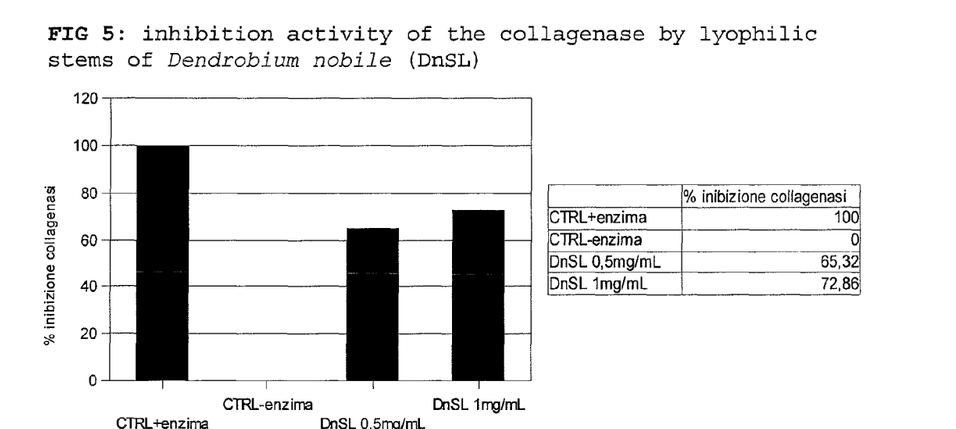
FIG. 5: activity of inhibition of the collagenase by lyophilized meristematic cells of *Dendrobium nobile* (DnSL)
Figure 6:
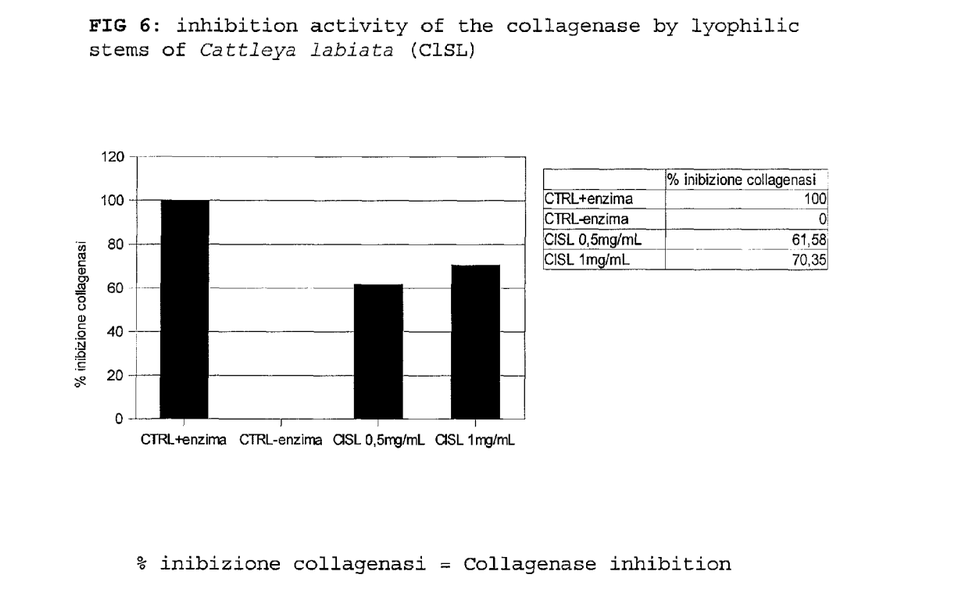
FIG. 6: activity of inhibition of the collagenase by lyophilized meristematic cells of *Cattleya labiata* (ClSL).

The results obtained by assaying a sample of lyophilized stems of *Dendrobium nobile* (DnSL) at the concentration of 0.1-1 mg/mL are reported in FIG. 5 and those obtained by assaying a sample of lyophilized stems of *Cattleya labiata* (ClSL) at the concentration of 0.1-1 mg/mL are reported in FIG. 6.

The preparations of the invention can be validly used for the following biological activities, with which they are provided:
  antioxidant activities, in the prevention and treatment of alterations connected with damage by free radicals with inflammatory component: skin alterations such as seborrheic, atopic and irritative dermatitis, cellulite, mucosal alterations including the mucous membranes of the oropharyngeal cavity, gastrointestinal and vaginal mucous membranes, dental alterations, alterations of the respiratory zone, articular pathologies, ophthalmic pathologies and diminished immune response;
  anti-inflammatory activities, in the prevention and treatment of alternations connected with chronic and acute inflammation states;
  cytoprotective activities, in the prevention of damage caused by environmental stress;
  activities of inhibition of the collagenase and stimulation of the collagen production in the prevention and treatment of skin disorders and for the slowing of skin aging processes;
  activities of inhibition of hyaluronidase, for the maintenance of skin tone, of hydration and for preventing and opposing skin relaxation.

In order to strengthen, modulate, synergize or amplify the above-mentioned spectrum of biological activities, mixtures of two or more preparations of the invention can be provided for in ratios that can vary between 1:10 and 10:1 of one preparation with respect to the other, in accordance with the needs and in particular with the biological activities that are wished to be maximized.

Therefore, forming a further object of the invention are preparation compositions that can be obtained from a preparation as defined above or from a mixture of two or more preparations as defined above.

The doses, times and administration path of the treatment are selected as a function of the type, stage, gravity and manifestation zone of the alteration. For all of the abovementioned alterations, oral administration is indicated as is topical, transdermal administrations—in any case, such to render the active principles especially available. For oral formulations, administrations are favored in tablet, pill or capsule form, but also as powders and suspensions: for topical treatments, gels, creams and ointments are preferred along with solutions compatible with dermal and mucosal use, in addition to collyria for administrations in the conjunctival sac.

The applied dose of the composition varies between 0.1 mg and 2 g per day and preferably between 5 mg and 150 mg per day, in single administration or in 2-4 doses or by means of slow-release forms as a function of the treatment needs of the subject and for periods that can vary from 1 and 120 days.

The same compositions, at suitable concentrations, can be formulated in supplement form to be taken orally, in the prevention or as coadjuvant treatment of alterations traceable to non-reactive human conditions. The compositions of the invention, at suitable concentrations and in suitable formulations, can also be used in cosmetics and in trichological treatments.

The invention claimed is:

1. Selected cell culture of meristematic cells of plants belonging to the *Dendrobium, Phalaenopsis, Ansellia, Polyrrhiza, Vanilla, Cattleya* or *Vanda* genera, characterized in that it contains a quantity of phenylpropanoids greater than 0.1% expressed on dry cell weight and a quantity of hydrosoluble polysaccharides greater than 5% expressed on the dry cell weight.

2. Cell culture according to claim 1, wherein said plants belong to the species *Dendrobium polysema, Dendrobium farmeri, Dendrobium nobile, Phalaenopsis aphrodite, Phalaenopsis hybrida, Ansellia africana, Polyrrhiza lindenii, Vanilla planifolia, Cattleya labiata* and *Vanda coerulea*.

3. Cell culture according to claim 1, characterized in that it contains an extensin quantity greater than 0.01% expressed on the dry cell weight.

4. Cell culture according to claim 1, wherein the quantity of said phenylpropanoids is greater than 1% expressed on the dry cell weight.

5. Cell culture according to claim 1, wherein said quantity of hydrosoluble polysaccharides is greater than 10% expressed on the dry cell weight.

6. Cell culture according to claim 3, wherein said extensin quantity is greater than 0.05% expressed on the dry cell weight.

7. Cell culture according to claim 1, wherein said hydrosoluble polysaccharides comprise glucomannans, xyloglucans, arabinogalactans, hemicellulose and pectins based on D-galacturonic units.

8. Cell culture according to claim 3, wherein said extensins comprise monomer extensins.

9. Cell culture according to claim 1, obtainable by a process which comprises:
   1) selecting clones deriving from the cultures of a stable cell line of plants belonging to the *Dendrobium, Phalaenopsis, Ansellia, Polyrrhiza, Vanilla, Cattleya* or *Vanda* genera in which maximized quantities of phenylpropanoids, hydrosoluble polysaccharides and optionally extensins are present;
   2) collecting plant biomass deriving from a cell culture of said clones selected according to step 1) on liquid culture terrain;
   3) separating the cells from the liquid culture terrain;
   4) optionally, lyophilization and/or spray-drying of said cells or solution or suspension of said cells in glycerol or in glycerol added with xanthan gum in a quantity variable from 0.1 to 2% W/W, or in a quantity equal to 0.3%, or in butylene glycol.

10. Cell culture according to claim 1, wherein said cell culture comprises a stabilized cell line of said plants.

11. Cell culture according to claim 4, wherein the quantity of said phenylpropanoids is greater than 10% expressed on the dry cell weight.

12. Cell culture according to claim 5, wherein said quantity of hydrosoluble polysaccharides is greater than 20% expressed on the dry cell weight.

13. Cell culture according to claim 6, wherein said extensin quantity is greater than 0.1% expressed on the dry cell weight.

* * * * *

UNITED STATES PATENT AND TRADEMARK OFFICE
CERTIFICATE OF CORRECTION

PATENT NO. : 8,709,810 B2  
APPLICATION NO. : 13/294933  
DATED : April 29, 2014  
INVENTOR(S) : Giovanna Pressi et al.

Page 1 of 1

It is certified that error appears in the above-identified patent and that said Letters Patent is hereby corrected as shown below:

On the title page, Item (73), Assignee, change "I.R.B Istituto di Richerche Biotechnologiche S.r.l." to --I.R.B Istituto di Richerche Biotecnologiche S.r.l.--

Signed and Sealed this
Fourteenth Day of July, 2015

Michelle K. Lee
*Director of the United States Patent and Trademark Office*